United States Patent
Meister et al.

(10) Patent No.: US 9,895,537 B2
(45) Date of Patent: Feb. 20, 2018

(54) SNR ADJUSTED ENVELOPE SAMPLING FOR HEARING IMPLANTS

(71) Applicant: MED-EL Elektromedizinische Geraete GmbH, Innsbruck (AT)

(72) Inventors: Dirk Meister, Innsbruck (AT); Thomas Schwarzenbeck, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 15/178,635

(22) Filed: Jun. 10, 2016

(65) Prior Publication Data
US 2017/0001006 A1   Jan. 5, 2017

Related U.S. Application Data

(60) Provisional application No. 62/174,003, filed on Jun. 11, 2015, provisional application No. 62/215,187, filed on Sep. 8, 2015.

(51) Int. Cl.
*A61N 1/05* (2006.01)
*A61N 1/36* (2006.01)

(52) U.S. Cl.
CPC ..... *A61N 1/36032* (2013.01); *A61N 1/36036* (2017.08); *A61N 1/0541* (2013.01)

(58) Field of Classification Search
CPC .......... A61N 1/36032; A61N 1/0541
See application file for complete search history.

(56) References Cited

U.S. PATENT DOCUMENTS

| 6,219,580 B1 | 4/2001 | Faltys et al. |
| 6,594,525 B1 | 7/2003 | Zierhofer |
| 9,084,893 B2 * | 7/2015 | Vandali ............ A61N 1/36032 |
| 2012/0209351 A1 * | 8/2012 | Meister ............ A61N 1/36032 607/57 |

(Continued)

FOREIGN PATENT DOCUMENTS

WO   WO 2016/049403 A1   3/2016

OTHER PUBLICATIONS

Middlebrooks "Auditory Cortex Phase Locking to Amplitude-Modulated Cochlear Implant Pulse Trains," Journal of Neurophysiol, vol. 100, pp. 76-91, 2008.

(Continued)

*Primary Examiner* — William Levicky
(74) *Attorney, Agent, or Firm* — Sunstein Kann Murphy & Timbers LLP

(57) ABSTRACT

A signal processing system is described for a hearing implant system. A band pass filter bank processes an audio input signal to generate band pass signals. An implant signal processor processes the band pass signals to generate electrode stimulation signals. The processing includes: i. monitoring a key feature characteristic of the audio input signal, ii. using an original coding strategy to generate the electrode stimulation signals when the key feature is less than or equal to an initial value, and iii. using a different new coding strategy to generate the electrode stimulation signals when the key feature is greater than or equal to a coding change value. The implant signal processor automatically transitions from the original coding strategy to the new coding strategy over a transition period of time by adaptively changing the original coding strategy to become the new coding strategy.

18 Claims, 9 Drawing Sheets

(56) References Cited

U.S. PATENT DOCUMENTS

2014/0005746 A1 1/2014 Schleich et al.
2014/0200630 A1 7/2014 Mishra
2016/0015974 A1 1/2016 Milczynski
2016/0106980 A1 4/2016 Sürth et al.

OTHER PUBLICATIONS

Wilson et al., "Better speech recognition with cochlear implants," Letters to Nature, vol. 325, pp. 236-238, Jul. 18, 1991.
International Searching Authority, International Search Report—International Application No. PCT/US16/36799, dated Sep. 6, 2016, together with the Written Opinion of the International Searching Authority, 20 pages.

* cited by examiner

SNR ADJUSTED ENVELOPE SAMPLING FOR HEARING IMPLANTS

This application claims priority from U.S. Provisional Patent Application 62/174,003, filed Jun. 11, 2015, and from U.S. Provisional Patent Application 62/215,187, filed Sep. 8, 2015, both of which are incorporated herein by reference in their entireties.

TECHNICAL FIELD

The present invention relates to signal processing arrangements for hearing implants, and more particularly, to automatically transitioning speech coding strategies for cochlear implants.

BACKGROUND ART

As shown in FIG. 1, sounds are transmitted by a human ear from the outer ear 101 to the tympanic membrane (eardrum) 102, which moves the bones of the middle ear 103 (malleus, incus, and stapes) that vibrate the oval window and round window openings of the cochlea 104. The cochlea 104 is a long fluid-filled duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolus where the spiral ganglion cells of the acoustic nerve 113 reside. In response to received sounds transmitted by the middle ear 103, the cochlea 104 functions as a transducer to generate electric pulses which are transmitted to the cochlear nerve 113, and ultimately to the brain which perceives the neural signals as sound.

Hearing is impaired when there are problems in the ability to transduce external sounds into meaningful action potentials along the neural substrate of the cochlea 104. To improve impaired hearing, auditory prostheses have been developed. In some cases, hearing impairment can be addressed by a cochlear implant (CI), a brainstem-, midbrain- or cortical implant that electrically stimulates auditory nerve tissue with small currents delivered by multiple electrode contacts distributed along an implant electrode. For cochlear implants, the electrode array is inserted into the cochlea 104. For brain-stem, midbrain and cortical implants, the electrode array is located in the auditory brainstem, midbrain or cortex, respectively.

FIG. 1 shows some components of a typical cochlear implant system where an external microphone provides an audio signal input to an external signal processor 111 which implements one of various known signal processing schemes. For example, signal processing approaches that are well-known in the field of cochlear implants include continuous interleaved sampling (CIS) digital signal processing, channel specific sampling sequences (CSSS) digital signal processing, spectral peak (SPEAK) digital signal processing, fine structure processing (FSP) and compressed analog (CA) signal processing.

The processed signal is converted by the external signal processor 111 into a digital data format, such as a sequence of data frames, for transmission by an external coil 107 into a receiving stimulator processor 108. Besides extracting the audio information, the receiver processor in the stimulator processor 108 may perform additional signal processing such as error correction, pulse formation, etc., and produces a stimulation pattern (based on the extracted audio information) that is sent through electrode lead 109 to an implanted electrode array 110. Typically, the electrode array 110 includes multiple stimulation contacts 112 on its surface that provide selective electrical stimulation of the cochlea 104.

An audio signal, such as speech or music, can be processed into multiple frequency band pass signals, each having a signal envelope and fine time structure within the envelope. One common speech coding strategy is the is the so called "continuous-interleaved-sampling strategy" (CIS), as described by Wilson B. S., Finley C. C., Lawson D. T., Wolford R. D., Eddington D. K., Rabinowitz W. M., "Better speech recognition with cochlear implants," Nature, vol. 352, 236-238 (July 1991), which is hereby incorporated herein by reference. The CIS speech coding strategy samples the signal envelopes at predetermined time intervals, providing a remarkable level of speech understanding merely by coding the signal envelope of the speech signal. This can be explained, in part, by the fact that auditory neurons phase lock to amplitude modulated electrical pulse trains (see, for example, Middlebrooks, J. C., "Auditory Cortex Phase Locking to Amplitude-Modulated Cochlear Implant Pulse Trains," J Neurophysiol, 100(1), p. 76-912008, 2008 July, which is hereby incorporated herein by reference).

However, both signal cues, the envelope and the final time structure, are important for normal hearing subjects (see, for example, Zeng F., Nie K., Stickney G., Kong Y., "Auditory Perception with Slowly-Varying Amplitude and Frequency Modulations," In: D. Pressnitzer, A. de Cheveigń e, S. McAdams, and L. Collet, "Auditory Signal Processing: Physiology, Psychoacoustics, and Models, Springer Verlag, New York, pp. 237-243, 2004, which is hereby incorporated herein by reference).

Older speech coding strategies mainly encode the slowly varying signal envelope information and do not transmit the fine time structure of a signal. More recent coding strategies, for example, Fine Structure Processing (FSP), also transmit the fine time structure information. In FSP, the fine time structure of low frequency channels is transmitted through Channel Specific Sampling Sequences (CSSS) that start at negative to positive zero crossings of the respective band pass filter output (see U.S. Pat. No. 6,594,525, which is incorporated herein by reference). The basic idea of FSP is to apply a stimulation pattern, where a particular relationship to the center frequencies of the filter channels is preserved, i.e., the center frequencies are represented in the temporal waveforms of the stimulation patterns, and are not fully removed, as is done in CIS. Each stimulation channel is associated with a particular CSSS, which is a sequence of ultra-high-rate biphasic pulses (typically 5-10 kpps). Each CSSS has a distinct length (number of pulses) and distinct amplitude distribution. The length of a CSSS may be derived, for example, from the center frequency of the associated band pass filter. A CSSS associated with a lower filter channel is longer than a CSSS associated with a higher filter channel. For example, it may be one half of the period of the center frequency. The amplitude distribution may be adjusted to patient specific requirements.

For illustration, FIG. 2A-2B show two examples of CSSS for a 6-channel system. In FIG. 2A, the CSSS's are derived by sampling one half of a period of a sinusoid whose frequency is equal to the center frequency of the band pass filter (center frequencies at 440 Hz, 696 Hz, 1103 Hz, 1745 Hz, 2762 Hz, and 4372 Hz). Sampling is achieved by means of biphasic pulses at a rate of 10 kpps and a phase duration of 25 µs. For Channels 5 and 6, one half of a period of the center frequencies is too short to give space for more than one stimulation pulse, i.e., the "sequences" consist of only one pulse, respectively. Other amplitude distributions may be utilized. For example, in FIG. 2B, the sequences are derived by sampling one quarter of a sinusoid with a frequency, which is half the center frequency of the band pass filters. These CSSS's have about the same durations as the CSSS's in FIG. 2A, respectively, but the amplitude distribution is monotonically increasing. Such monotonic distributions might be advantageous, because each pulse of the sequence can theoretically stimulate neurons at sites which cannot be reached by its predecessors.

FIG. 3 illustrates a typical signal processing implementation of the FSP coding strategy. The audio signal is first split up into spectral bands by means of a filter bank of band pass filters 301. Each of these spectral bands is then further processed by a zero crossing detector 303 that detects the negative to positive zeros crossings of each spectral band. The CSSS 305 are inserted at the start of the negative to positive zero crossings of their respective band pass filter output. An envelope detector 307 provides the envelopes of band pass time signals, which include unresolved harmonics and are modulated with the difference tones of the harmonics, mainly the fundamental frequency F0. When the CSSS stimulation pulses are weighted 309 with these envelopes, the resulting pulses are undesirably amplitude modulated mainly with F0. This also applies to the frequency bands that are designed to transmit fine time structure, in addition to amplitude cues.

SUMMARY

Embodiments of the present invention are directed to systems and methods for signal processing in a hearing implant system that has an implanted electrode array with multiple stimulation contacts for delivering electrode stimulation signals to adjacent auditory neural tissue. A band pass filter bank is configured for processing an audio input signal to generate multiple band pass signals which represent associated bands of audio frequencies in the audio input signal. An implant signal processor is configured for processing the band pass signals to generate the electrode stimulation signals. This processing includes: i. monitoring a key feature characteristic of the audio input signal, ii. using an original coding strategy to generate the electrode stimulation signals when the key feature is less than or equal to an initial value, and iii. using a different new coding strategy to generate the electrode stimulation signals when the key feature is greater than or equal to a coding change value. The implant signal processor is configured for automatically transitioning from the original coding strategy to the new coding strategy over a transition period of time during which the implant signal processor adaptively changes the original coding strategy to become the new coding strategy.

In specific embodiments, one of the coding strategies may be an event-based coding strategy while the other coding strategy is an envelope-based coding strategy. In addition or alternatively, one of the coding strategies may use adaptive stimulation pulse rates while the other coding strategy uses constant stimulation rates. For example, the implant signal processor may be configured to use an adaptive stimulation pulse rate based on channel specific sampling sequences (CSSS), and adaptively increases the CSSS pulse sequence length to transition to a constant stimulation rate coding strategy. Or, the implant signal processor may be configured to use time intervals during which no pulse is applied to transition to a constant stimulation rate coding strategy.

The implant signal processor may specifically be configured for automatically transitioning either while the key feature changes from the initial value to the coding change value, or after. And the key feature may be a signal to noise ratio (SNR) of the audio input signal or a direct to reverberation ratio (DRR) of the audio input signal.

DETAILED DESCRIPTION

Parameters of a given cochlear implant signal coding strategy might not be optimal for all listening conditions. For example, in noisy conditions some coding strategies might perform better than others since temporal fine structure typically is more affected by noise than is the band pass signal envelope. It would be beneficial to switch from one coding strategy to another, depending on listening conditions. The switching could be performed in small increments so that the transition happens in a smooth morphing from one coding strategy to the other. The audio input signal is monitored and analyzed to estimate one or more key features that are present. Based on the key feature(s), the signal coding strategy is automatically modified.

As an example of a key feature, the signal to noise ratio (SNR) of the audio input signal can be estimated. It is assumed that event-based coding strategies that transmit temporal fine structure of the input signal (such as FSP by MED-EL) are optimal in relatively quiet listening conditions, while envelope-based coding strategies (such as HD-CIS by MED-EL are better in noisier conditions. A smooth transition can then be made automatically from FSP to HD-CIS based on the SNR of the audio input signal by modifying the length and the shape of the channel-specific sampling sequences (CSSS) that are used for the output stimulation pulses.

Figure 1:
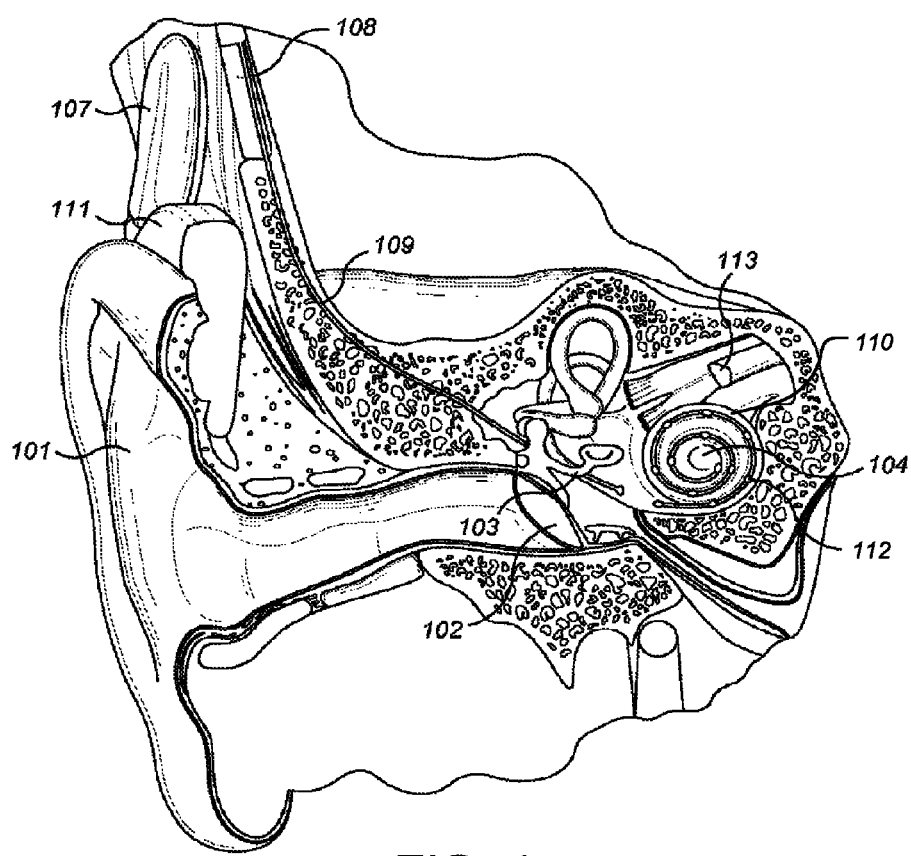
FIG. 1 shows anatomical structures of a human ear and some components of a typical cochlear implant system.
Figure 2:
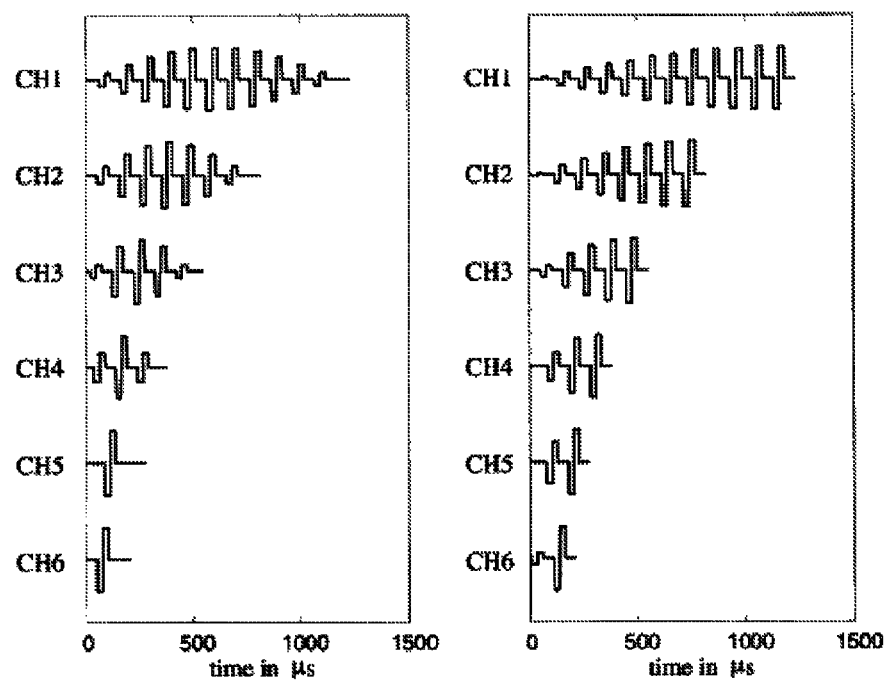
FIGS. 2A and 2B show channel specific sampling sequences (CSSS) for two 6-channel systems utilizing biphasic pulses at 10 kpp/s and phase duration of 25 µs.
Figure 3:
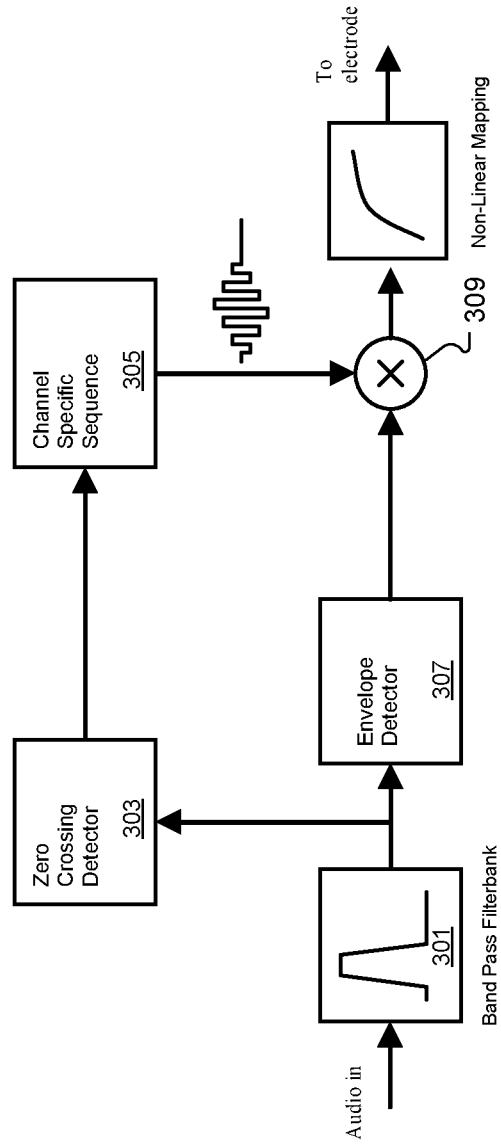
FIG. 3 shows various functional blocks in a prior art fine structure processing (FSP) signal processing arrangement.
Figure 4:
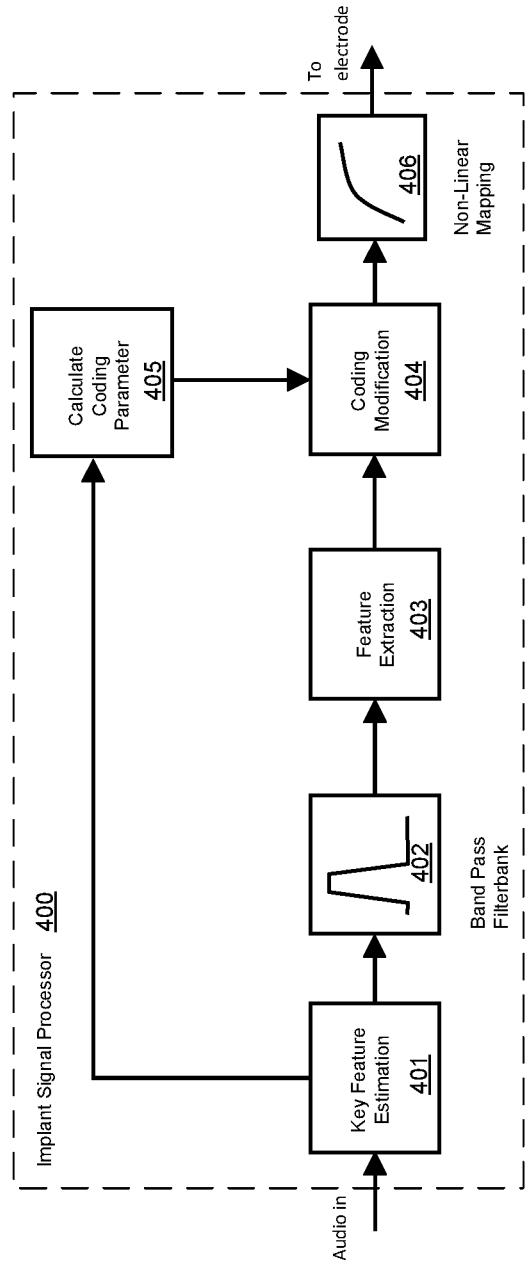
FIG. 4 shows various functional blocks in a coding modification signal processing arrangement according to an embodiment of the present invention.

FIG. 4 shows various functional blocks in a generic coding modification signal processing arrangement for a hearing implant system that has an implanted electrode array with multiple stimulation contacts for delivering electrode stimulation signals to adjacent auditory neural tissue. The implant signal processor 400 uses an FSP approach and includes a key feature estimation module 401 that monitors one or more key features in an audio input signal that reflects the current hearing environment. A conventional band pass filter bank 402 processes the audio input signal to generate multiple band pass signals which each represent associated bands of audio frequencies in the audio input signal.

A feature extraction module 403 processes the band pass signals from the band pass filter bank 402 to extract the band pass envelopes and fine structure time information and generate an initial set of stimulation pulses for the stimulation contacts according to an original coding strategy. For example, the original coding strategy may be an event-based coding strategy such as FSP that uses adaptive stimulation rates according to the fine structure information in the band pass signals.

A coding parameter module 405 monitors the key feature from the key feature estimation module 401 and so long as value of the key feature is less than or equal to some given initial value, the coding modification block 404 passes along the stimulation pulses as produced by the feature extraction module 403 according to the original coding strategy. At some point when the key feature is greater than or equal to a coding change value, the coding parameter module 405 controls the coding modification block 404 to begin adjusting the stimulation pulses to adaptively change the original coding strategy over a transition period of time to automatically transition to the new coding strategy. For example, the new coding strategy may be an envelope-based coding strategy such as CIS or HD-CIS that uses stimulation pulses at a constant stimulation rate. The implant signal processor 400 may specifically be configured for automatically transitioning either while the key feature changes from the initial value to the coding change value, or after. A non-linear mapping module 406 then adjusts the amplitude of the output stimulation pulses using anon-linear mapping that provides patient-specific scaling and data stream generation.

Figure 5:
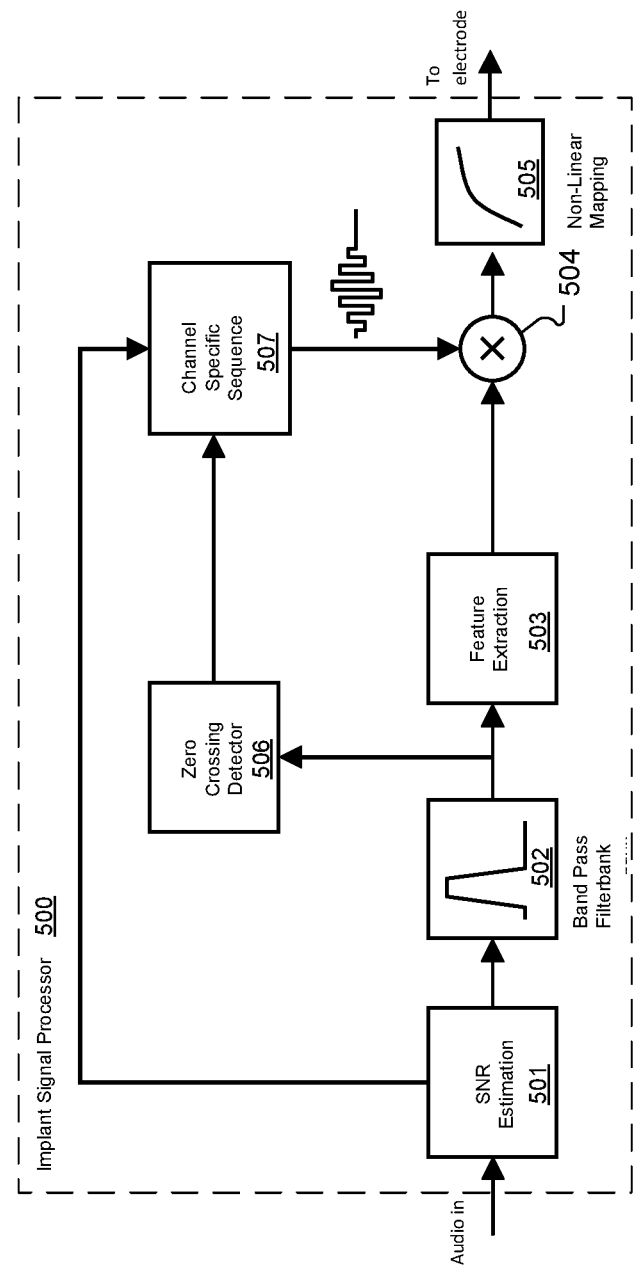
FIG. 5 shows various functional blocks in a specific embodiment of the present invention using SNR as the key feature with CSSS.

FIG. 5 shows various functional blocks in an embodiment of the present invention where the implant signal processor 500 uses SNR as the key feature with CSSS pulse sequences. An SNR estimation module 501 that monitors one or more key features in the input signal, while a band pass filter bank 502 processes the audio input signal to generate the band pass signals. A zero crossing detector 506 detects the negative to positive zeros crossings of each band pass signal (the temporal fine structure information). A channel specific sequence module 507 creates CSSS output timing request pulses at the start of the negative to positive zero crossings of each band pass signal, while a feature extraction module 503 derives the band pass signal envelopes. The pulse weighting module 504 weights (amplitude modulates) the CSSS stimulation pulses with the band pass envelopes, which is then further adjusted by the non-linear mapping module 505 that provides patient-specific scaling and data stream generation.

At each zero crossing trigger event from the zero crossing detector 506, the channel specific sequence module 507 determines an event-specific length for the CSSS pulse sequence ("FL interval"). The pulse weighting module 504 shapes the CSSS pulse sequence to follow the band pass envelope amplitude so that the band pass envelope is sampled with the CSSS sequence. When the SNR signal from the SNR estimation module 501 is relatively high (quiet sound environment), the channel specific sequence module 507 adjusts the FL interval to be so short that a CSSS pulse sequence may consist of as little as a single pulse. As the SNR signal from the SNR estimation module 501 decreases (the environment becomes noisier), the channel specific sequence module 507 increases the FL interval and adds more pulses to the CSSS sequence until at some point for a low SNR (high noise), the last pulse of the CSSS sequence is seamlessly followed by the first pulse of the next CSSS sequence, resulting in a continuous (constant rate) sampling of the band pass envelopes from the feature extraction module 503. If the length of the FL interval becomes larger than the time between two consecutive trigger events (i.e., two zero crossings), the channel specific sequence module 507 may terminate the existing CSSS sequence when the next trigger event occurs and the FL interval of the following trigger event overrules the previous FL interval. Or the channel specific sequence module 507 may continue with the CSSS pulse sequence initiated by the first trigger event and ignore the subsequent trigger event so that the end of the existing FL interval, a new FL interval is determined. Once the SNR signal from the SNR estimation module 501 increases again, the channel specific sequence module 507 adaptively adjusts the FS interval to again become shorter than the times between the trigger events.

Figure 6:
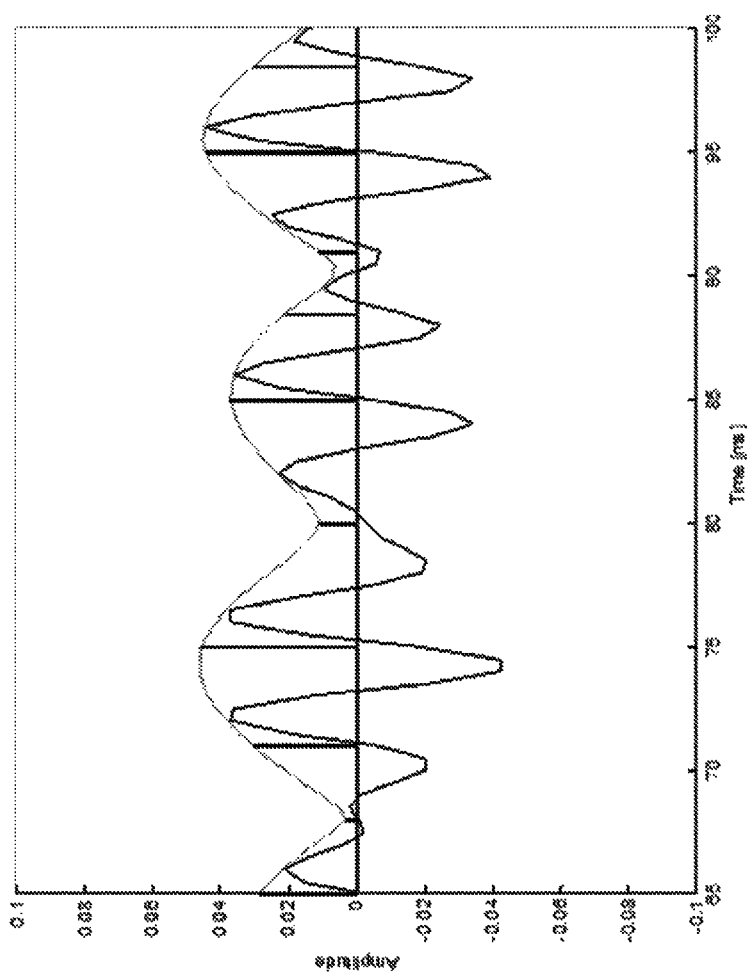
FIG. 6 shows an example of a processed band pass signal and the resulting CSSS pulse sequence for a vowel with added Gaussian noise and a SNR=10 dB.
Figure 7:
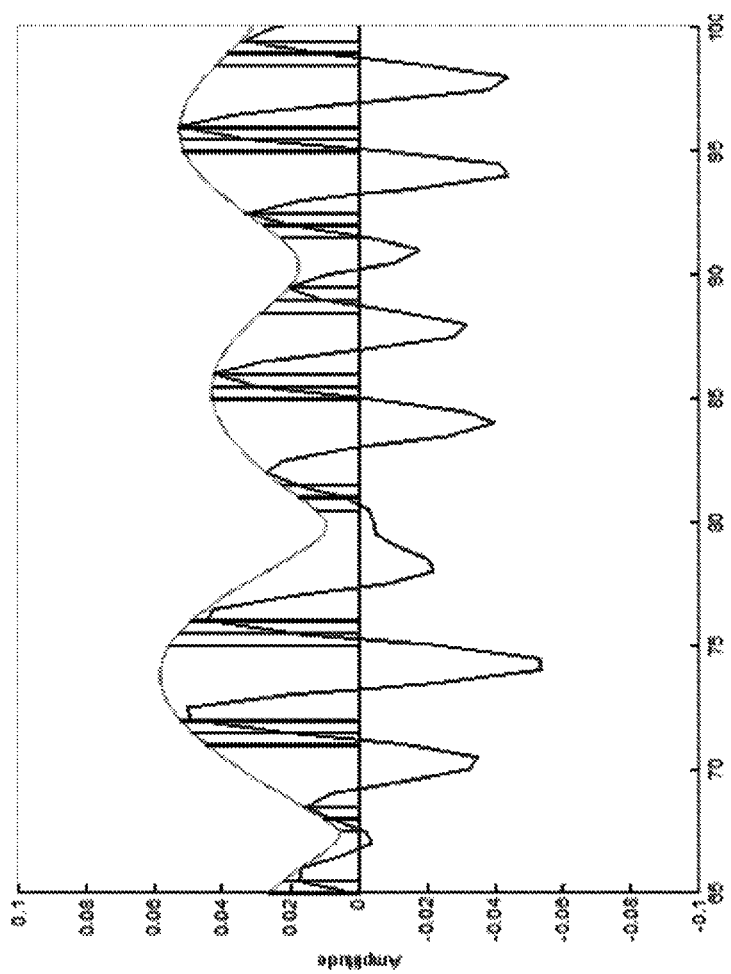
FIG. 7 shows the same signal as in FIG. 6, with SNR=5 dB.
Figure 8:
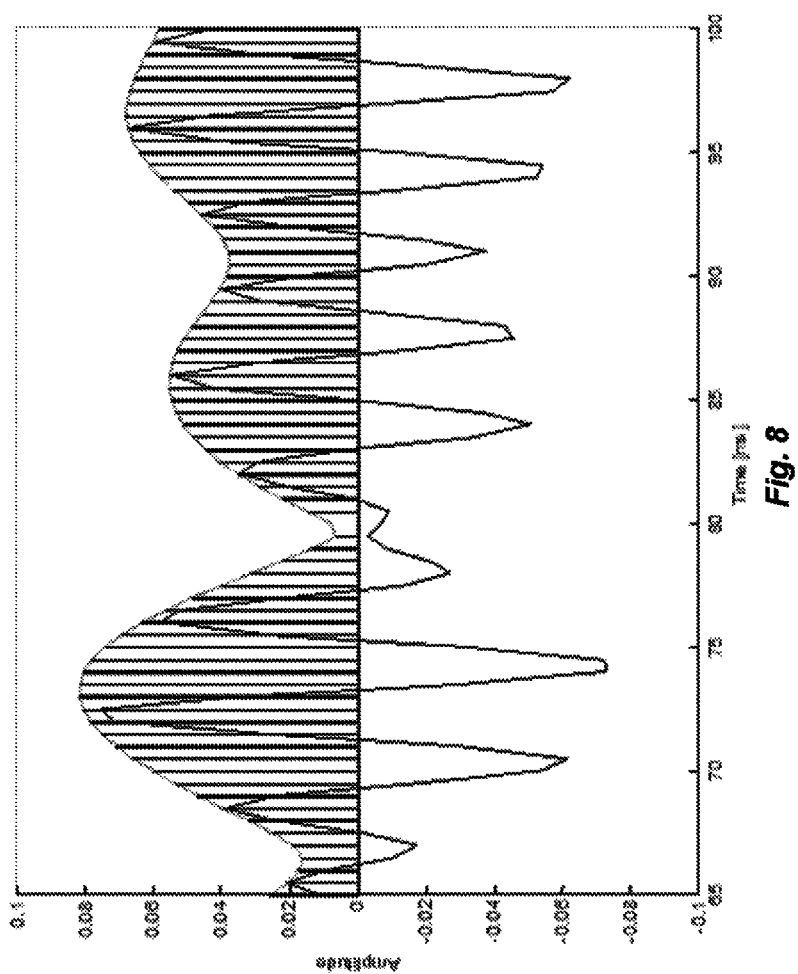
FIG. 8 shows the same signal as in FIG. 6, with SNR=0 dB.

FIG. 6 shows an example of a processed band pass signal and the resulting CSSS pulse sequence for a vowel with added Gaussian noise and a SNR=10 dB. The band pass signal is the higher frequency full sine wave signal in dark gray, the Hilbert band pass envelope is the slower varying half sine wave trace shown in light gray, and the vertical black lines represent the applied CSSS sequences with a sequence length of one. FIG. 7 shows the same signal as in FIG. 6, when the SNR signal decreases down to 5 dB (more noise) and the FL interval is increased so that the CSSS sequences contain three pulses each. FIG. 8 shows the same signal as in FIG. 6, with SNR=0 dB (noisier still) where the FL interval is so long that the CSSS sequence performs a continuous sampling of the band pass envelope that is similar to the HD-CIS coding strategy.

In addition to or alternatively to adaptively varying the length of the CSSS interval, other specific embodiments may adaptively control other signal variables. For example, in combination with the application of a CSSS pulse at a specific event (e.g. a zero crossing event), a subsequent time interval—FS-interval—may be determined within which a pulse has to be applied. The length of this FS-interval may be determined by the value of the SNR signal at the time when the pulse has been applied: If the SNR is high, the FS-interval may be chosen to be long, while if the SNR is low, the FS-interval may be chosen to be short. To restrict the stimulation rate to a maximum value that reflects the refractory period of the auditory nerve fibers, a shortest possible FS-interval can be defined that corresponds to the maximum stimulation rate. There are several different specific possibilities:

If another timing event occurs within the FS-interval determined from the previous timing event, and the time between the two timing events is greater than the refractory period, then a pulse can be applied at the second timing event and a new FS-interval is initiated that overrules the previous one.

If another timing event occurs within the FS-interval determined from the previous timing event, but the time between the two timing events is shorter than the refractory period, then a pulse can be applied at the end of the refractory period and a new FS-interval is initiated that overrules the previous one.

If no additional timing event appears before the end of the current FS-interval and the refractory period is shorter than the FS-interval, then another pulse can be applied (forced) at the end of the FS-interval.

If no additional timing event appears before the end of the current FS-interval interval, but the refractory period is greater than the FS-interval, then another pulse can be applied (forced) at the end of the refractory period.

In general, an embodiment may require that a subsequent pulse (either caused by the occurrence of a timing event or by the end of the FS-interval) can only be applied if a minimum period (e.g. the refractory period) is over. In some applications, it may be advantageous to have a shorter period than the refractory period as the minimum period.

Figure 9:
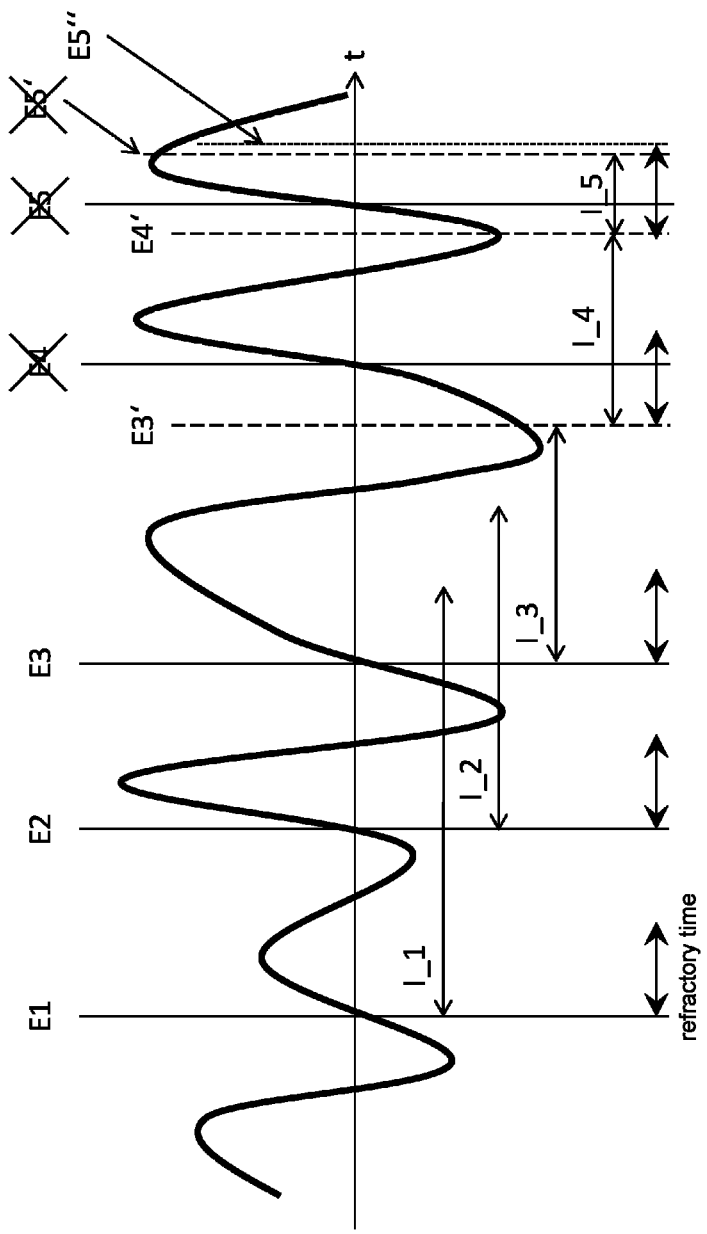
FIG. 9 shows an example of a processed band pass signal and SNR-adapted pulse time intervals according to an embodiment of the present invention.

FIG. 9 shows an example of a processed band pass signal and SNR-adapted pulse time intervals according to an embodiment of the present invention. In FIG. 9, it is assumed that five zero crossing timing events E1-E5 (vertical solid lines) are detected, the SNR is decreasing over time t (i.e. from left to right), and the refractory period is as shown by the corresponding horizontal arrows across the bottom the figure denoted as "refractory time". The first CSSS pulse is, without limitation, applied at the zero crossing event E1. Since the SNR is high, the corresponding FS-interval I_1 is relatively long. The next zero crossing event E2 occurs before the end of the I_1 FS-interval, so the next CSSS pulse is applied at E2, and the same situation with I_2 and E3 although the SNR has meantime decreased so that I_2 is shorter than I_1. However, at the event E3' that occurs at the end of the I_3 FS-interval, a CSSS pulse is forced because no further zero crossing has occurred within this FS-interval starting after zero crossing event E3 (also the refractory time (after E3) is still shorter than I_3). The next zero crossing event occurs at E4, but that is still within the refractory period after the last applied pulse at E3' so there is no pulse applied at E4 nor is any corresponding FS-interval determined. Similarly, at E5 no pulse is applied, and in addition, at E4' the SNR is so low that the corresponding I_5 FS-interval is determined to be shorter than the refractory period so at E5', no pulse is applied but instead is delayed until E5" corresponding to the end of the refractory period after event E4'.

When the SNR later increases more and more (not shown in FIG. 9) the FS-intervals will again become longer and longer until a zero crossing event will be detected after the end of the refractory time but before the end of an FS-interval. From that point on, the zero crossing events will again determine the pulse sequence and the coding strategy follows the known event-based coding strategies until the SNR decreases again. The maximum stimulation rate can be set to be proportional to the inverse of the minimum possible interval (e.g. the refractory period) so that the instantaneous stimulation rate (which equals 1/FS-interval) cannot exceed a given defined value; e.g. a typical rate as presently used for CIS or HD-CIS coding strategies. In general, the lower the SNR, the more the resulting sound coding sequence will be according to an envelope-based coding strategy such as CIS or HD-CIS (constant sampling of each channel in a prescribed manner with the defined maximum stimulation rate). The higher the SNR, the more the resulting sound coding sequence will be like according to a pure event-based coding strategy such as FSP.

The MCL and THR values may vary when switching from one specific coding strategy to another, so the MCL and THR values of the patient-specific scaling function should also be adjusted (in addition to the CSSS sequence) to promote a loudness-balanced transition between the different coding strategies.

The modification of the CSSS sequences can also be done channel-wise, i.e. based on channel-specific SNR values. And while the foregoing was described with SNR being the parameter for subsequent adaptive modifications, other specific signal parameters that characterize the quality of an existing hearing situation may be used as well; e.g. the direct to reverberation ratio (DRR).

Both approaches—variation of CSSS lengths and determination of time intervals within which no pulse is applied—yield similar overall results: a smooth transition between event-based (variable rate) and envelope-based (constant rate) coding strategies. Embodiments of the present invention adapt the sound coding strategy to changes in the sound environment with optimal settings for each environment. With SNR-adjusted sampling, temporal fine structure is provided in situations where it is not disturbed, while the sound coding is morphed seamlessly to a more noise-robust envelope coding for better sound perception in noisier environments.

Embodiments of the invention may be implemented in part in any conventional computer programming language such as VHDL, SystemC, Verilog, ASM, etc. Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A signal processing system comprising a hearing implant system having an implanted electrode array with a plurality of stimulation contacts for delivering electrode stimulation signals to adjacent auditory neural tissue, the signal processing system comprising:

a band pass filter bank configured for processing an audio input signal to generate a plurality of band pass signals each representing an associated band of audio frequencies in the audio input signal; and an implant signal processor configured for processing the band pass signals to generate the electrode stimulation signals, wherein the processing includes:
  i. monitoring a key feature characteristic of the audio input signal,
  ii. using an original coding strategy to generate the electrode stimulation signals when the key feature is less than or equal to an initial value,
  iii. using a different new coding strategy to generate the electrode stimulation signals when the key feature is greater than or equal to a coding change value, and
  iv. delivering the electrode stimulation signals to the stimulation contacts in the implanted electrode array;
wherein the implant signal processor is configured for automatically transitioning from the original coding strategy to the new coding strategy over a transition period of time during which the implant signal processor adaptively changes the original coding strategy to become the new coding strategy.

2. The signal processing system according to claim 1, wherein one of the coding strategies is an event-based coding strategy and one of the coding strategies is an envelope-based coding strategy.

3. The signal processing system according to claim 1, wherein one of the coding strategies uses adaptive stimulation pulse rates and one of the coding strategies uses constant stimulation rates.

4. The signal processing system according to claim 3, wherein the implant signal processor is configured to use an adaptive stimulation pulse rate based on channel specific sampling sequences (CSSS), and wherein the implant signal processor is configured to adaptively increase CSSS pulse sequence length to transition to a constant stimulation rate coding strategy.

5. The signal processing system according to claim 3, wherein the implant signal processor is configured to transition to a constant stimulation rate coding strategy using time intervals during which no pulse is applied.

6. The signal processing system according to claim 1, wherein the implant signal processor is configured for automatically transitioning after the key feature changes from the initial value to the coding change value.

7. The signal processing system according to claim 1, wherein the implant signal processor is configured for automatically transitioning while the key feature changes from the initial value to the coding change value.

8. The signal processing system according to claim 1, wherein the key feature is a signal to noise ratio (SNR) of the audio input signal.

9. The signal processing system according to claim 1, wherein the key feature is a direct to reverberation ratio (DRR) of the audio input signal.

10. A method of signal processing comprising a hearing implant system having an implanted electrode array with a plurality of stimulation contacts for delivering electrode stimulation signals to adjacent auditory neural tissue, the method comprising:

processing an audio input signal with a band pass filter bank to generate a plurality of band pass signals each representing an associated band of audio frequencies in the audio input signal; and processing the band pass signals to generate the electrode stimulation signals, wherein the processing includes:
  i. monitoring a key feature characteristic of the audio input signal,
  ii. using an original coding strategy to generate the electrode stimulation signals when the key feature is less than or equal to an initial value, and
  iii. using a different new coding strategy to generate the electrode stimulation signals when the key feature is greater than or equal to a coding change value, and
  iv. delivering the electrode stimulation signals to the stimulation contacts in the implanted electrode array;
wherein the processing automatically transitions from the original coding strategy to the new coding strategy over a transition period of time during which the original coding strategy is adaptively changed to become the new coding strategy.

11. The method according to claim 10, wherein one of the coding strategies is an event-based coding strategy and one of the coding strategies is an envelope-based coding strategy.

12. The method according to claim 10, wherein one of the coding strategies uses adaptive stimulation pulse rates and one of the coding strategies uses constant stimulation rates.

13. The method according to claim 12, wherein the adaptive stimulation pulse rate coding strategy is based on channel specific sampling sequences (CSSS), and wherein CSSS pulse sequence length is adaptively increased to transition to a constant stimulation rate coding strategy.

14. The method according to claim 12, wherein the processing transitions to a constant stimulation rate coding strategy using time intervals during which no pulse is applied.

15. The method according to claim 10, wherein the automatic transitioning occurs after the key feature changes from the initial value to the coding change value.

16. The method according to claim 10, wherein the automatic transitioning occurs while the key feature changes from the initial value to the coding change value.

17. The method according to claim 10, wherein the key feature is a signal to noise ratio (SNR) of the audio input signal.

18. The method according to claim 10, wherein the key feature is a direct to reverberation ratio (DRR) of the audio input signal.

* * * * *